United States Patent [19]

Fogel et al.

[11] Patent Number: 4,511,652

[45] Date of Patent: Apr. 16, 1985

[54] HIGH EFFICIENCY EUKARYOTIC METALLOTHIONEIN PROMOTER SYSTEM

[75] Inventors: Seymour Fogel; Juliet W. Welch, both of Kensington; Michael Karin, San Francisco, all of Calif.

[73] Assignee: The Regents of the University of California, Berkeley, Calif.

[21] Appl. No.: 384,821

[22] Filed: Jun. 3, 1982

[51] Int. Cl.³ .................. C12Q 1/29; C12P 21/00; C12P 21/02; C12P 19/34; C12N 15/00; C12N 1/20; C12N 1/16; C12N 1/18; C12N 1/00; C07H 21/04
[52] U.S. Cl. ........................................ 435/29; 435/68; 435/70; 435/91; 435/172.3; 435/253; 435/255; 435/256; 435/317; 536/27; 935/11; 935/19; 935/34; 935/37; 935/69; 935/79; 935/84
[58] Field of Search .................. 435/68, 70, 91, 172, 435/253, 255, 256, 317, 29, 172.3; 536/27

[56] References Cited

U.S. PATENT DOCUMENTS 4,387,162  6/1983  Aigle et al. .................. 435/253

OTHER PUBLICATIONS

Struhl et al., Proc. Natl. Acad. Sci. USA 76, 1035 (1979).
Lerch: Proceedings of the First International Meeting on Metallothionein and Other Low Molecular Weight Metal-Binding Proteins, Zurich, Jul. 17–22, 1978, Kagi et al. (Ed.), 1979.
Lewin: Genes, John Wiley & Sons, New York, 1983, p. 679.
Beach and Palmiter, Proc. Natl. Acad. Sci. USA, (1981), 78:2110–2114.
Brenes-Pomales et al., Nature, (1955), 176:841–842.
Mortimer and Fogel, in Mechanisms in Recombination, R. Grell, Ed., (Plenum Press, NY), pp. 263–275.

Primary Examiner—Lionel M. Shapiro
Assistant Examiner—James Martinell
Attorney, Agent, or Firm—Bertram I. Rowland

[57] ABSTRACT

Yeast metallothionein (copper chelatin) and DNA sequences having the gene encoding the polypeptide are provided. The DNA sequences find use in producing copper chelatin and in amplifying downstream flanking regions.

18 Claims, No Drawings

HIGH EFFICIENCY EUKARYOTIC METALLOTHIONEIN PROMOTER SYSTEM

BACKGROUND OF THE INVENTION

1. Field of the Invention

The capability of manipulating DNA sequences encoding a polypeptide has greatly expanded the ability to synthesize a wide variety of polypeptides of commercial and physiological interest, as well as to modify the capability and functioning of cells. Unicellular microorganisms can be used to prepare a wide variety of polypeptides which naturally occur in mammals. In employing the unicellular microorganisms, it is desirable to enhance the production of the product of interest as compared to the total protein produced by the cell. In this manner, the cost of the product can be substantially reduced in relation to the cost of maintenance and growth of the microorganisms. Therefore, there have been many approaches in devising ways to enhance expression of the product of interest.

Of the unicellular microorganisms, yeast provides many advantages for the production of polypeptides employing recombinant or hybrid DNA technology. There already exists a large body of developed technology for the use of yeast in fermentation and for the production of many chemicals of commercial interest. Thus, conditions, growth, media, and methods of purification are already available.

Yeast are safe organisms and have been industrially used for an extended period of time, so that the handling and disposal is well established. Yeast are eukaryotic, rather than prokaryotic. Therefore, yeast are more likely to have analogous mechanisms for expression and more efficiently recognize the codons of a gene associated with a higher mammalian source.

In employing yeast for the production of polypeptides exogenous to the yeast, it is desirable that maximized production of the polypeptides of interest is achieved subject to limitations on the viability of the yeast. One technique which has encouraged higher yields of polypeptides of interest in a foreign host has been the use of multicopy plasmids. Multicopy plasmids suffer from a number of deficiencies, not least of which is that one must produce a large amount of DNA and the substances associated with the maintenance and replication of such DNA due to the multiple copies of the genes on the multicopy plasmid. Thus a substantial amount of the host's energy is dedicated to the production of products of no interest to the host or the manufacturer.

Another technique is to employ a highly efficient promoter, particularly a host promoter which is associated with the natural production of a polypeptide which is present as a high percentage of the total protein of the host or provides a high transcription turnover rate.

A third technique is to provide a way which amplifies the gene of interest. This technique has involved the use of a gene and its regulatory system which responds to stress by multiplication of the gene. It is found that by joining a foreign gene as a flanking region to the stress amplifiable gene, multiple repeats occur which will include both genes.

2. Description of the Prior Art

Kagi and Nodberg, Eds. (1979) Metallothionein (Birkhauser, Basel) and Beach and Palmiter, Proc. Natl. Acad. Sci., U.S.A. (1981) 78:210-214 describe metallothioneins generally. Brenes -Pomales et al, Nature (1955) 176: 841-842 describe copper sensitive and copper resistant yeast strains. These polymorphisms were then studied extensively as markers in investigating gene conversion. Mortimer and Fogel (1974) In; Mechanisms in Recombination, R. Grell, Ed. (Plenum Press, New York) Pages 263-275, is illustrative of these studies. See also PCT application Nos. U.S. 81/00239 and U.S. 81/00240.

SUMMARY OF THE INVENTION

A novel yeast gene system is provided which expresses a copper chelating polypeptide (Cu-chelatin) having a high cysteine content, in addition to high percentages of polar amino acids, such as lysine, glutamic acid, and serine. The gene system finds use in amplification of other genes flanking the chelatin gene, so as to provide for tandem and non-tandem iterated copies of the flanking gene, by selecting for a copper resistant yeast host. The multiple copies of the flanking genes can be used for expression of a polypeptide of interest.

DESCRIPTION OF THE SPECIFIC EMBODIMENTS

Techniques are provided for the enchanced production of a copper chelating metallothionein, which is naturally found in copper resistant yeast strains. Isolation of the gene encoding the copper chelating polypeptide (copper or Cu-chelatin) in combination with its regulatory functions, provides a DNA segment which can be used in a wide variety of ways and for a wide variety of purposes.

The DNA segment can be introduced into a yeast host to provide for copper resistance to the yeast host. The DNA segment can also be introduced into a yeast host, which then may be stressed with copper resulting in amplification of the gene and its regulatory system, for enchanced production of Cu-chelatin. The gene by itself or in combination with its regulatory system, can be introduced into a foreign host e.g., a prokaryote, to provide for copper resistance. Of particular interest is the use of the Cu-chelatin system in conjunction with another gene as the down stream flanking region of the Cu-chelatin gene.

A eukaryotic host capable of expressing the Cu-chelatin is transformed with the DNA segment containing the Cu-chelatin gene and the associated flanking gene. The DNA segment may be tandemly integrated and/or non-tandemly integrated numerous times by repetitively enhancing the copper concentration of the medium. In this way one selects for clones of organisms which remain viable at the elevated copper concentrations. These viable organisms are associated with repeats of the Cu-chelatin gene in conjunction with the associated flanking genes. Thus, both the Cu-chelatin and the flanking genes may be expressed in substantial amounts in the host.

Finally, Cu-chelatin itself may find use as a chelating agent for removing heavy metals, particularly copper, from a wide variety of waste or other types of industrial streams.

In summation, the subject invention involves nucleic acid sequences which encode for Cu-chelatin, or such sequence in conjunction with yeast regulatory signals for Cu-cheltain, a nucleic acid sequence which includes the Cu-chelatin gene as well as a second gene, where the entire sequence is capable of iteration, tandemly or non-tandemly, in the presence of heavy metal, particularly copper; and, the protein Cu-chelatin or effective analogs and fragments thereof. The polynucleotide sequences described above may find use by themselves, in conjunction with other polynucleotide sequences as an extrachromosomal element or integrated into a yeast chromosome.

The DNA sequence encoding for Cu-chelatin can be obtained by partial digestion of the yeast chromosomal DNA from a copper resistant yeast strain. Various restriction enzymes may be used for the partial digestion, providing fragments of about 10 to 30 kbp. The resulting DNA fragments may then be cloned employing an appropriate vector, particularly one having a prokaryotic replicon. Desirably, shuttle vectors are employed, where the DNA segments may be amplified in a prokaryotic host, the plasmid isolated and purified, and then used for transformation of a yeast host.

Desirably copper sensitive host cells, either wild type or mutants, are employed which allow for selection of transformants or tranductants of the host having copper resistance. One may then select for copper resistant transformed hosts, isolating the resulting yeast clones and subjecting the copper resistant host to increasing concentrations of copper in the nutrient medium. Conveniently, the copper concentration can be increased incrementally from a low of about 0.1 mM copper, usually at least about 0.3 mM to a concentration of less than about 20 mM copper, usually a concentration of less than about 15 mM copper. Increments will generally vary from about 0.2 mM to 5 mM. In order to survive at these elevated copper concentrations, the modified host will require multicopy genes encoding for Cu-chelatin.

By isolating the plasmid from the modified host transformed from copper sensitive to copper resistant, where the DNA segment is inserted into a particular restriction site of the expression vector, the DNA segment may be excised and denatured to provide single strands, which can then be used as hybridization probes. These probes can be used to demostrate the presence of the Cu-chelatin gene intergrated into the chromosome. Conveniently, the probes are labeled to provide a detectable signal. Various labels include radionuclides, combinations of ligands or receptors, where one is bound to the hybridization probe and the other is multiply labeled e.g. biotin and avidin, enzymes, flourescers, and the like.

The gene encoding yeast Cu-chelatin has fewer than about 300 bp. Even in combination with the regulatory signals associated with transcription and translation of the gene, this segment will generally be less than about 600 bp. Upon stressing a host into which the Cu-chelatin gene has been introduced, in conjunction with its regulatory signals, the tandemly iterated DNA segment is found to be about 1 to 2 kbp, so that more than about 1 kbp can be added as a downstream flanking region to the Cu-chelatin gene to be tandemly iterated in conjunction with the Cu-chelatin gene.

The second gene may be ligated to the downstream end of the Cu-chelatin gene. The second gene will have its own regulatory system, including a promoter, other transcriptional regulatory signals, as well as a ribosomal start site recognized by the yeast host. Desirably, a strong promoter will be used, that is, a promoter which is associated with a polypeptide product present in large amounts in the yeast. Of particular interest are such promoters as PGK ADH, etc. promoters.

The 3'-terminus of the RNA sequence coding for yeast Cu-chelatin can be readily determined from the amino acid sequence at the carboxy terminus of yeast Cu-chelatin. The polypeptide is sequenced by conventional techniques and a plurality of probes prepared based on the redundancy of codons for the amino acids. Where a convenient restriction site is not available downstream from the Cu-chelatin gene, one can be introduced by mutagenesis. Alternatively, one can use primer repair for removing the nucleotides downstream from the Cu-chelatin gene, providing a double stranded DNA segment having blunt ends. The DNA segment encoding for Cu-chelatin and including the regulatory sequences may be ligated to the second gene. The resulting segment having the two genes may then be inserted into an appropriate expression vector and clones selected which have the desired DNA sequences in the proper orientation.

Tandem iteration in conjunction with non-tandem iteration may then be achieved by growing the yeast cells at sequentially increased concentrations of copper in the range of about 0.3 mM to about 20 mM, more usually up to about 15 mM, with incremental increases as previously indicated.

Modified cells having the tandem iteration of the Cu-chelatin gene and other gene may then be selected and grown for expression of the two genes. In this way, high yields of a desired product may be achieved.

The yields can be further enchanced by employing multicopy vectors, and/or by having multiple integration of the gene into the host, so that random iteration occurs at a plurality of chromosomal sites. One may then select for hosts having a high number of repeat units.

Integration into the chromosome can be achieved by associating with the DNA segment containing the Cu-chelatin gene and other gene, an additional sequence which is analgous to a DNA sequence found at at least one, preferably at a plurality of sites in the chromosome. In this way, through recombination, the entire construct of the DNA namely regulatory signals and genes encoding for the Cu-chelatin gene and other gene may be inserted at a plurality of sites into the yeast genome.

Alternatively, one can employ a minichromosome, involving a yeast centromere, at least one autonomously replicating segment (ars) and the Cu-chelatin and other gene construct. The minichromosome can be stably maintained in the yeast host, without selective conditions.

For the most part, regardless of the manner in which the Cu-Chelatin is introduced into the yeast host, the yeast host will be grown under selective conditions to ensure the maintenance of high copy numbers of the Cu-chelatin gene.

As compared to other copper chelating compounds found previously, the Cu-chelatin found in yeast has a molecular weight of about 6500 d. The amino acid composition is comprised of about 16% cysteine, 10% lysine, 10% glutamic acid, 11% serine, and about 8% each of asparagine, glutamine, threonine, and glycine. The remaining amino acids are present in less than about 5 number percent.

The following is the amino acid sequence for yeast Cu-chelatin, the nucleotide sequence encoding for Cu-chelatin, the polypeptide product having molecular weight of about 6490.

| met | phe | ser | glu | leu | ile | asn | phe |
|-----|-----|-----|-----|-----|-----|-----|-----|
| ATG | TTC | AGC | GAA | TTA | ATT | AAC | TTC |
|     |     | 10  |     |     |     |     |     |
| gln | asn | glu | gly | his | glu· | cys | gln |
| CAA | AAT | GAA | GGT | CAT | GAG | TGC | CAA |
|     |     |     | 20  |     |     |     |     |
| cys | gln | cys | gly | ser | cys | lys | asn |
| TGC | CAA | TGT | GGT | AGC | TGC | AAA | AAT |
|     |     |     |     |     |     | 30  |     |
| asn | glu | gln | cys | gln | lys | ser | cys |
| AAT | GAA | CAA | TGC | CAA | AAA | TCA | TGT |
| ser | cys | pro | thr | gly | val | thr | ala |
| AGC | TGC | CCA | ACG | GGT | GTA | ACA | GCG |
| 40  |     |     |     |     |     |     |     |
| ala | thr | thr | met | pro | cys | gly | asn |
| GCG | ACG | ACA | ATG | CCC | TGC | GGT | AAC |
|     |     |     | 50  |     |     |     |     |
| lys | ser | glu | glu | thr | lys | lys | ser |
| AAG | TCT | GAA | GAA | ACC | AAG | AAG | TCA |
| cys | cys | ser | gly | lys |     |     |     |
| TGC | TGC | TCT | GGG | AAA |     |     |     |

The gene of interest is flanked by restriction sites of the following restriction endonucleases while lacking such restriction sites in the coding region: Taq1, Rsa I, Hinf I, Dde I. Thus, the segment encoding for the Cu-Chelatin gene can be readily isolated substantially free of non-coding regions.

The following description is offered by of illustration and not by way of limitation.

EXPERIMENTAL

Materials and Method

Strains and DNAs

DNA transformations were performed with the haploid *Saccharomyces cerevisiae* strain, BZ31-1-7Ba, carrying the following auxotrophic markers: trpl-289, ura3-52, ade8-18, arg4-16, cup1$^s$. Copper resistance (CUP1$^r$) genes were selected from a pool of hybrid DNA prepared by Nasmyth and Reed, Proc. Natl. Acad. Sci., U.S.A. (1980) 77:2119–2123. This pool was prepared from a Sau-3A partial digest of AB320 yeast DNA cloned into the BamH1 site of the plasmid YRp7. The genomic DNA used in the construction of this hybrid pool was prepared from strain AB320 (HO, ade2-1, lys2-1, trp5-2, leu2-1, can1-100, ura3-1, met4-1). This strain is a segregant from hybrid W87 (Rothstein et al, Genetics (1977) 85:35-54) and it probably is closely related to haploid X2180. *E. coli* strain HB101 was used for transfections.

The YRp7 vector is a pBR322 derivative that carries a 1.43 kb EcoR1 segment comprising the TRP1+yeast gene and sequences capable of conferring autonomous replication in yeast (arsl). The YRp17 vector contains the URA3+yeast gene at the Aval site of pBR322, as well as the 1.43 kb TRP1+EcoR1 fragment.

Cultivation of Microorganisms

*E. coli* was grown in LB-medium (Davis et al, (1980) Advanced Bacterial Genetics: A Manual for Genetic Engineering (Cold Spring Harbor Labl, Cold Spring Harbor, N.Y.)). Ampicillin was added (50 ug/ml) when plasmid containing cells were grown. Yeast culture conditions and handling followed previously published procedures (Fogel et al (1981) in, Microbiology of the Yeast Saccharomyces, Strathem et al eds. (Cold Spring Harbor, N.Y.)). Copper medium (0.3 mM CuSO$_4$) is a synthetic complete medium solidified with 1.5% phytagar (Gibco Labs, Grand Island, N.Y.)

DNA Transformations and Preparations

Yeast transformations were according to Hinnen's procedures (Hinnen et al, PNAS (1978) 75:1929-1933) with the following exception: after resuspension in 1M sorbitol and 50 mM NaPO$_4$ pH 7.5, cells were treated with 0.1% β-mercaptoethanol and 40 units/ml lyticase at 30° C. for 1 hour. *E. coli* transformations were performed in accordance with the procedures described by Davis et al, supra, and Wesink et al, Cell (1974) 3:315–325. Rapid DNA preparations are according to Struhl et al, Proc. Natl. Acad. Sci., U.S.A. (1979) 76:1035–1039. DNA subcloning procedures are according to Davis et al, supra.

Agarose gels (0.7%) were prepared in 40 mM tris-OH, 20mM acetic acid, 2mM Na$_2$EDTA pH 8.2 containing 0.5 μg/ml ethidium bromide and electrophoresed in a horizontal apparatus at 1–1.5 V/cm. DNA bands were retrieved from gels by electrophoretic collection on Whatman DE 81 filters (Winberg and Hammarskjold, Nucl. Acids. Res. (1980) 8:253–265. Elution in 1M NaCl was followed by ethanol precipitation. Genomic DNAs for DNA-DNA hybridization were prepared according to Struhl, et al, supra, electrophoresed on 0.5% agarose gels and transferred to cellulose nitrate as in Southern's procedure. These were hybridized with a nick translated $^{32}$P labelled probe prepared from the 1.25 kb Sau3A DNA fragment.

Notation

YJW9,10,11 denote yeast strains containing plasmids pJW6,9,10,or 11, respectively. The cloned DNA sequences are designated JW6,9,10 and 11 corresponding to the inserts contained within the plasmids.

Results

The copper sensitive (cup1$^s$) recipient haploid yeast strain BZ31-7Ba was transformed to TRP1+with the Sau3A-partial yeast DNA bank contained in the YRp7 vector. This pool is described in Materials and Methods. Of nearly 500 TRP1+transformant colonies, twelve grew confluently when transferred to 0.3 mM copper plates, a concentration completely inhibitory to the growth of the recipient yeast strain BZ31-1-7Ba. Insert-bearing plasmids, autonomously replicating in yeast, were detected in four isolates: YJW6, YJW9, YJW10, and YJW11, and these were subsequently used to transform *E. coli*. The resultant ampicillin resistant-tetracycline sensitive bacteria were grown for large scale plasmid preparations. Plasmid DNAs were analysed by restriction endonuclease digestion.

One inserted fragment (pJW6) was cleaved by three enzymes: HindIII, XbaI, and KpnI. Located 50 base pairs (bp) away from the left-most Kpn1 site, the unique HindIII restriction site defines one terminus of the iterated segment within the cloned DNA fragment. The pJW6 digests prepared with XbaI and KpnI displayed two bands on agarose gels which sum to less than the lengths of the insert and the YRp7 vector. In addition, the two bands produced with pJW9, 10 and 11 do not have equimolar intensities. Although a linear of pJW6 is 12.1 kb in length, i.e., 5.8 kb (vector)+6.3 kb (insert), in both the XbaI and KpnI digests the observed bands sum to only 8.15 kb (6.2 kb and 1.95 kb). In addition, digestion with the restriction endonuclease Sau3A yields 0.7 and 1.25 kb restriction fragments which are in molar excess compared to the vector DNA fragments. Similarly, electrophoresis of DdeI and DpnI restriction enzyme digests also exhibit unique non-vector bands of increased fluoresence intensity.

To account for these collective observations, as well as the high frequency of copper resistant colonies among transformants, i.e., about 2%, it is believed that the chromosomal region controlling the level of copper resistance is composed of tandemly iterated 1.96 kb DNA segments. Each repeat unit contains single KpnI and XbaI sites along with two Sau3A-DpnI sites containing methylated adenine residues.

The remaining three plasmids (pJW9, pJW10, and pJW11) include DNA inserts that also confer resistance to copper. Their electophoretic patterns are similar to that displayed by pJW6. However, plasmids pJW9 and pJW11 contain longer, non-repetitious DNA segments that extend beyond the terminal HindIII site. Within the repeat sequence there are no sites for the following restriction enzymes: AvaI, BamHI, BglIII, EcoRI, HaeIII, HindII, HindIII, HpaI, PstI, PvuII, SalI, SstI. Taken collectively, the present data based on restriction enzyme mapping, indicate that the cloned DNA fragments capable of conferring resistance to copper in $S.$ $cerevisie$ embrace three and a fraction of a fourth repetitive 1.95 kb units.

In order to delineate the smallest DNA fragment that would impart resistance to elevated copper concentrations, several DNA fragments were subcloned. The 1.25 kb Sau3A restriction fragment constituting less than one basic repeat unit and the 1.95 kb XbaI fragment, one repeat unit, were collected from pJW10 digests. When pJW11 is cleaved with EcoRI and BamHI, a 3.1 kb fragment of yeast DNA containing more than one repeat unit and 800 bp of non-repetitive DNA sequences is generated. These three DNA fragments were subcloned into the vector YRp17 (URA3+, TRP1+ and ARS1+) and used to transform a copper-sensitive (cup1$^s$) yeast strain (BZ31-1-7ba) to TRP1+ and URA3+.

In each instance, the recipient cells, transformed to TRP1+ and URA3+ displayed resistance to 0.3 mM copper. When the transformed yeast cells were grown under nonselective conditions, they exhibited the phenotypic instability associated with autonomously replicating plasmids, i.e. high frequencies of cup1$^s$, trp1$^-$, ura3$^-$ cells were regenerated. Resistance to copper ions can be achieved by the presence of the 1.25 kb Sau3A DNA fragment. The copper resistance phenotype appears to be associated only with that fragment.

Several integrations of the cloned copper resistant DNA regions into yeast chromosomal DNA were isolated. The first, a 3.1 kb (JW11, EcoR1-BamHI) DNA fragment, recloned into YRp17, integrated near the ura3-52, site close to the chromosome V centromere via the URA3 sequence present in the vector molecule. The second, pJW10, integrated at trp1-289, and the third, pJW9, recombined at the cup1 site on chromosome VIII. This presumptive integrant was crossed to a strain genetically marked on chromosome VIII by the presence of thr1. The resultant diploid was sporulated and 61 unselected asci were subjected to tetrad analysis.

The markers cup1$^s$ and trp1 co-segregated 2+:2− in all tetrads. Complete linkage was observed for these markers and recombinants between them were not detected. This behavior is expected if a DNA fragment bearing the CUP1$^r$ locus, inserted into the YRp7 plamid containing TRP1+, integrated near the cup1 site. Parental ditypes (PD), nonparental ditypes (NPD), and tetratypes (T), respectively 30:0:31, were found for either CUP1 and THR1 or for TRP1 and THR1.

Five additional independent integrations of pJW10 were crossed and a total of 84 unselected asci were analyzed. The PD:NPD:T ratio for these same markers was 37:0:47. The complete absence of nonparental ditypes in a combined total sample of 145 tetrads (67:0:78) provides a clear indication of gene-gene linkage and the calculated map distance between CUP1 or TRP1 and THR1 is 27 cM, an estimate well within the sampling limits of the published value of 28 cM (Mortimer and Schild, Microbiol. Rev. (1980) 44:519-571). These data establish that the cloned DNA fragments confer a stable copper resistance phenotype on cup1 sensitive recipient cells, and that they contain functional segments of the CUP1$^r$ locus located distal to the thr1 marker in chromosome VIII.

An analysis by Southern's DNA-DNA hybridization method was conducted using a nick translated $^{32}$P labeled probe prepared from the 1.25 kb Sau3A DNA fragment to determine copy number. Genomic DNA prepared from copper sensitive and copper resistant yeast cells was digested with EcoRI, a restriction enzyme which has no cleavage sites within the repeat unit. The cup1$^s$ strain carries a hybridizable segment of 5 kb, maximally 2 repeat units, compared to about 30 kb or about 15 tandemly iterated repeat units in X2180, a CUP1$^r$ strain.

In accordance with the subject invention, DNA sequences are available which provide for production of a heavy metal chelating compound, called copper chelatin, which is capable of expression in yeast and other organisms. In addition, by stressing the host, downstream flanking regions can be tandemly reiterated in the host, either on an extrachromosomal element or integrated into the chomosome, so as to provide for multicopies, not only of the gene encoding copper chelatin, but also the accompanying flanking region. By having the accompanying flanking region encoding a polypeptide of interest, and having its own regulatory signals, the polypeptide of interest will also be expressed. In this manner, by varying the heavy metal concentration, one can select, enhance or reduce expression of a gene associated with the metallothionein gene.

Although the foregoing invention has been described in some detail by way of illustration and example for purposes of clarity of understanding, it will be obvious that certain changes and modifications may be practiced within the scope of the appended claims.

What is claimed is:

1. A DNA sequence encoding yeast copper chelatin or a copper chelating fragment thereof having naturally occurring flanking regions, each flanking region being less than 5 kbp.

2. A DNA sequence according to claim 1, comprising the naturally occurring yeast expression regulatory signals for expression upstream from the sequence encoding yeast copper chelatin.

3. A DNA sequence according to claim 2, comprising regulatory signals for expression recognized by the yeast host and a gene encoding a polypeptide foreign to a yeast host downstream from said gene encoding said yeast copper chelatin.

4. A DNA sequence according to claim 3, wherein said gene encoding said yeast copper chelatin and said foreign gene and their regulatory signals encompass a total number of nucleotides of less than 2 kbp.

5. A multi-copy DNA sequence having tandem iterations of a DNA sequence according to any of claims 1, 2, or 4.

6. A DNA sequence comprising a pair of expression regulatory signals recognized by a yeast host separated by a gene encoding yeast copper chelatin and a foreign gene under the regulatory control and downstream from the downstream regulatory signals and having a flanking sequence of at least 100 bp substantially homologous to a portion of a yeast chromosome.

7. A DNA sequence according to claim 6, wherein said flanking region is homologous to a chromosomal portion coding for an enzyme involved in a metabolic process.

8. An extrachromosomal construct comprising a yeast replicon, regulatory signals recognized by yeast for expression and under the control of said regulatory signals, a gene encoding for yeast copper chelatin.

9. An extrachromosomal construct according to claim 8, comprising: (a) second expression regulatory signals recognized by yeast, said second expression regulatory signals being downstream from said yeast copper chelatin gene; and (b) a gene encoding a polypeptide foreign to yeast under the control of said second regulatory signals, wherein said foreign gene is less than 1 kb from the terminal codon of said gene encoding for yeast copper chelatin.

10. An extrachromosomal construct according to claim 9, wherein said regulatory signals and said two genes encompass a DNA segment of not more than 2 kbp.

11. An extrachromosomal construct according to any of claims 9 or 10, wherein said regulatory genes and said two genes are tandemly iterated.

12. An extrachromosomal construct according to claim 11, wherein said iteration is at least 15 units.

13. A yeast cell having an extrachromosomal construct according to any of claims 8, 9 or 10.

14. A yeast cell having iterated DNA sequences of: (a) first expression regulatory signals; (b) a gene encoding for yeast copper chelatin; (c) second expression regulatory signals; and (d) a gene foreign to said yeast cell, wherein said genes are under the regulatory control of the proximal regulatory signals and said regulatory signals are recognized by said yeast cell.

15. A yeast cell according to claim 14 wherein at least a portion of said iterated sequences are present on an extrachromosomal DNA element.

16. A yeast cell according to claim 14, wherein at least a portion of said iterated sequences are present in a chromosome.

17. A yeast cell according to any of claims 14, 15 or 16 having at least 15 iterations.

18. In a method for detecting yeast cells modified by introduction of a DNA segment containing a gene capable of expression in said yeast host;

the improvement which comprises having as part of said DNA segment, a gene expressing yeast copper chelatin capable of expression in said yeast; and selecting for yeast cells resistant to copper.

* * * * *